US012642503B2

(12) United States Patent
Liao et al.

(10) Patent No.: US 12,642,503 B2
(45) Date of Patent: Jun. 2, 2026

(54) NEEDLE FREE DELIVERY SYSTEM AND OPERATION METHOD THEREOF

(71) Applicants: National Taiwan University of Science and Technology, Taipei City (TW); NATIONAL TAIWAN UNIVERSITY, Taipei (TW); National Defense Medical University, Taipei (TW)

(72) Inventors: Ai-Ho Liao, Taipei City (TW); Chih-Hung Wang, New Taipei City (TW); Hao-Li Liu, Taipei City (TW)

(73) Assignees: National Taiwan University of Science and Technology, Taipei City (TW); NATIONAL TAIWAN UNIVERSITY, Taipei (TW); National Defense Medical University, Taipei (TW)

( * ) Notice: Subject to any disclaimer, the term of this patent is extended or adjusted under 35 U.S.C. 154(b) by 993 days.

(21) Appl. No.: 17/661,564

(22) Filed: May 1, 2022

(65) Prior Publication Data

US 2023/0233181 A1      Jul. 27, 2023

(30) Foreign Application Priority Data

Jan. 27, 2022    (TW) ................................. 111103785

(51) Int. Cl.
A61B 8/00          (2006.01)
A61M 11/00        (2006.01)
            (Continued)

(52) U.S. Cl.
CPC ......... A61B 8/4444 (2013.01); A61M 11/005 (2013.01); A61M 37/0092 (2013.01);
            (Continued)

(58) Field of Classification Search
CPC ......... A61B 8/4444; A61B 8/12; A61B 8/481; A61B 8/4488; A61B 8/4494; A61B 8/00;
            (Continued)

(56) References Cited

U.S. PATENT DOCUMENTS 5,135,001 A * 8/1992 Sinofsky ................ A61B 8/445
                                                            600/459
6,312,383 B1 11/2001 Lizzi et al.
            (Continued)

FOREIGN PATENT DOCUMENTS

CN          103736180 A       4/2014
CN          105013547 A       11/2015
            (Continued)

OTHER PUBLICATIONS

Ai-Ho Liao et al., "Development of a thermosensitive poloxamer 407-based microbubble gel with ultrasound mediation for inner ear drug delivery", Drug Delivery, vol. 28, No. 1, Jun. 18, 2021, 1256-1271.

(Continued)

*Primary Examiner* — Bhisma Mehta
*Assistant Examiner* — Fatimata Sahra Diop
(74) *Attorney, Agent, or Firm* — CKC & Partners Co., LLC

(57)                ABSTRACT

The present disclosure provides a needle free delivery system, which includes a handheld device and a signal switching device. The signal switching device is electrically connected to the handheld device, and the handheld device includes an ultrasonic probe. The signal switching device provides a burst wave capable of generating a resonant carrier wave through piezoelectric material to the handheld device, so that an ultrasonic wave of the handheld device can perform a needleless delivery on a carrier.

18 Claims, 10 Drawing Sheets

102

(51) Int. Cl.
  *A61M 37/00* (2006.01)
  *H04R 17/10* (2006.01)
  *A61N 7/00* (2006.01)
(52) U.S. Cl.
  CPC ............... *H04R 17/10* (2013.01); *A61N 7/00* (2013.01); *A61N 2007/0039* (2013.01)
(58) Field of Classification Search
  CPC . A61M 11/005; A61M 37/0092; H04R 17/10; A61N 7/00; A61N 2007/0039
  See application file for complete search history.

(56) References Cited

U.S. PATENT DOCUMENTS

| | | | | |
|---|---|---|---|---|
| 9,149,658 | B2 * | 10/2015 | Barthe | ..................... A61N 7/00 |
| 9,789,109 | B2 | 10/2017 | Liao et al. | |
| 9,974,787 | B2 | 5/2018 | Liao et al. | |
| 2003/0009153 | A1 * | 1/2003 | Brisken | ............. A61M 37/0092 |
| | | | | 604/890.1 |
| 2006/0195077 | A1 * | 8/2006 | Kadziauskas | ......... B06B 1/0215 |
| | | | | 606/4 |
| 2009/0200395 | A1 * | 8/2009 | Duru | ..................... B05B 17/063 |
| | | | | 239/102.1 |
| 2016/0213256 | A1 * | 7/2016 | Li | ......................... A61B 5/0095 |
| 2017/0312490 | A1 * | 11/2017 | Unger | ............... A61M 37/0092 |
| 2017/0319835 | A1 * | 11/2017 | Ignon | ..................... A61B 17/50 |
| 2018/0235574 | A1 * | 8/2018 | Morimoto | ............. B06B 1/0207 |
| 2020/0156113 | A1 * | 5/2020 | Wuchinich | .......... B01F 23/2133 |
| 2021/0069529 | A1 * | 3/2021 | Capelli | .............. A61B 17/2251 |

FOREIGN PATENT DOCUMENTS

| | | |
|---|---|---|
| JP | 5801355 B2 | 10/2015 |
| TW | 200637621 A | 11/2006 |
| TW | I323196 B | 4/2010 |
| TW | I491409 B | 7/2015 |
| TW | I589306 B | 7/2017 |
| TW | I616210 B | 3/2018 |
| TW | 201920256 A | 6/2019 |
| TW | 202027865 A | 8/2020 |
| WO | 2017185695 A1 | 11/2017 |

OTHER PUBLICATIONS

Ai-Ho Liao et al., "Minoxidil-coated lysozyme-shelled microbubbes combined with ultrasound for the enhancement of hair follicle growth: Efficacy in vitro and in vivo", Frontiers in Pharmacology, Apr. 27, 2021, vol. 12: 668754.
Ai-Ho Liao et al., "Synergistic effects of combined treatment with ultrasound-mediated cisplatin-loaded microbubbles and atorvastatin on head and neck cancer", Head & Neck (Head and Neck—journal for the Sciences and Specialties of the Head and Neck), Sep. 21, 2020, 43(1):15-26.
Ai-Ho Liao et al., "Low-frequency dual-frequency ultrasound-mediated microbubbles cavitation for transdermal minoxidil delivery and hair growth enhancement", Scientific Reports, Mar. 9, 2020, 10(1), 4338.
Ai-Ho Liao et al., "Application of ultrasound-mediated adapalene-coated lysozyme-shelled microbubbles in UVA-induced skin photoaging", Plos One, May 21, 2020, 15(5): e0232617.
Ai-Ho Liao et al., "Ultrasound-induced microbubble cavitation via a transcanal or transcranial approach facilitates inner ear drug delivery" JCI Insight, Feb. 13, 2020, 5(3), pii: 132880.
Ai-Ho Liao et al., "Combining Microbubble Contrast Agent with Pulsed-Laser Irradiation for Transdermal Drug Delivery", Pharmaceutics, Oct. 4, 2018, 10, 175, 1-13.
Hang-Kang Chen et al., "Insonation of Systemically Delivered Cisplatin-Loaded Microbubbles Significantly Attenuates Nephrotoxicity of Chemotherapy in Experimental Models of Head and Neck Cancer", Cancers, Sep. 5, 2018, 10:311.

Ai-Ho Liao et al., "Ultrasound-Mediated EGF-Coated-Microbubble Cavitation in Dressings for Wound-Healing Applications", Scientific Reports, May 29, 2018, 8(1):8327.
Ai-Ho Liao et al., "Treatment effects of lysozyme-shelled microbubbles and ultrasound in inflammatory skin disease", Scientific Reports, Jan. 24, 2017, 7:41325.
Ai-Ho Liao et al., "Penetration depth, concentration and efficiency of transdermal α-arbutin delivery after Ultrasound Treatment with Albumin-Shelled Microbubbles in Mice", Drug Delivery, Jul. 30, 2014, 23(7), 2173-2182.
Engelke L. et al., "Recent insights into cutaneous immunization: How to vaccinate via the skin", Vaccine, May 23, 2015, 33(37):4663-4674.
Ravi AD et al., "Needle free injection technology: A complete insight", Int J Pharm Investig 2015, 5(4):192-199.
Gill HS et al., "Coated microneedles for transdermal delivery", J Control Release , Feb. 12, 2007, 117:227-237.
Lee JW et al., "Dissolving microneedles for transdermal drug delivery", Biomaterials, May 2008, 29:2113-2124.
Tezel A et al., "Low-frequency ultrasound as a transcutaneous immunization adjuvant", Vaccine, Mar. 16, 2005, 23:3800-3807.
Kushner JIV et al., "Dual-channel two-photon microscopy study of transdermal transport in skin treated with low-frequency ultrasound and a chemical enhancer", Journal of Investigative Dermatology, Jun. 7, 2007, vol. 127:2832-2846.
Tezel A et al., "Topical delivery of anti-sense oligonucleotides using low-frequency sonophoresis", Pharm Res, vol. 21, No. 12, Dec. 2004, 21:2219-2225.
Mitragotri S et al., "Transdermal drug delivery using low-frequency sonophoresis", Pharm Res, 1996, 13:411-420.
Dahlan A et al., "Transcutaneous immunisation assisted by low-frequency ultrasound", Int J Pharm, 2008, 368:123-128.
Choi EH et al., "Iontophoresis and sonophoresis stimulate epidermal cytokine expression at energies that do not provoke a barrier abnormality: lamellar body secretion and cytokine expression are linked to altered epidermal calcium levels", J Investig Dermatol, Jun. 19, 2003, vol. 121, No. 5:1138-1144.
Bhatnagar S et al., "Exploitation of sub-micron cavitation nuclei to enhance ultrasound-mediated transdermal transport and penetration of vaccines", J Control Release, Jul. 12, 2016, 238:22-30.
Melino S et al., "Molecular properties of lysozyme-microbubbles: towards the protein and nucleic acid delivery", Amino Acids, Nov. 18, 2011, 43(2):885-896.
Lee L et al., "Exploring new applications of lysozyme-shelled microbubbles", Langmuir, May 14, 2019, 35(31):9997-10006.
Zabner J et al., "Cellular and molecular barriers to gene transfer by a cationic lipid", J Biol Chem, Aug. 11, 1995, vol. 270, No. 32:18997-19007.
Guan W et al., "CT Findings of coronavirus disease (Covid-19) severe pneumonia", AJR Am J Roentgenol, May 2020, W1-W2.
Tian S et al., "Pulmonary pathology of early-phase 2019 novel coronavirus (Covid-19) pneumonia in two patients with lung cancer", J Thorac Oncol, vol. 15, No. 5, Feb. 28, 2020, pii: S1556-0864(20)30132-30135.
Soldati G et al., "Contrast-enhanced ultrasound in patients with Covid 19: pneumonia, acute respiratory distress syndrome, or something else?", J Ultrasound Med, Apr. 23, 2020, 12 : 10.1002/jum.15338.
Quarato CMI et al., "The role of transthoracic ultrasound in the novel coronavirus disease (Covid-19): a reappraisal. Information and disinformation: is there still place for a scientific debate?", Front Med (Lausanne), May 27, 2020, 7:271.
Patton JS, "Mechanisms of macromolecule absorption by the lungs", Adv. Drug Delivery Rev., 1996; 19:3-36.
Labiris NR et al., "Pulmonary drug delivery. part I: physiological factors affecting therapeutic effectiveness of aerosolized medications", Br. J. Clin. Pharmacol, Mar. 21, 2003, 56:588-599.
Sugiyama MG et al., "Lung ultrasound and microbubbles enhance aminoglycoside efficacy and delivery to the lung in E. coli-induced pneumonia and ARDS", Am J Respir Crit Care Med., Apr. 11, 2018, 198:404-408.

* cited by examiner

<u>100</u>

200

102

102

212

210

230

140

252

250

102

102

102

102

710

720

723

722

730

<u>800</u>

S801 using the signal switching device to provide a burst wave
capable of generating a resonant carrier wave through
a piezoelectric material for the handheld device

S802 using the handheld device to receive the burst wave
capable of generating the resonant carrier wave through
the piezoelectric material and to generate a burst wave
signal capable of generating a plurality of resonant
carrier waves with a plurality of ultrasonic frequencies
through a plurality of piezoelectric materials

NEEDLE FREE DELIVERY SYSTEM AND OPERATION METHOD THEREOF

This application claims priority to Taiwan Application Serial Number 111103785, filed Jan. 27, 2022, which is herein incorporated by reference.

BACKGROUND

Field of Invention

The present invention relates to systems and methods, and more particularly, a needle free delivery system and an operation method thereof.

Description of Related Art

An injection (often and usually referred to as a "shot" in US English) is the act of administering a liquid, especially a drug, into a person's body using a needle and a syringe.

Compared to traditional syringes, needle-free injection techniques cover a wide range. However, this technology still needs to be further improved in terms of convenience and efficiency.

SUMMARY

The following presents a simplified summary of the disclosure in order to provide a basic understanding to the reader. This summary is not an extensive overview of the disclosure and it does not identify key/critical components of the present invention or delineate the scope of the present invention. Its sole purpose is to present some concepts disclosed herein in a simplified form as a prelude to the more detailed description that is presented later.

According to embodiments of the present disclosure, the present disclosure provides needle free delivery systems and operation methods thereof, to solve or circumvent aforesaid problems and disadvantages in the related art.

An embodiment of the present disclosure is related to a needle free delivery system including a handheld device and a signal switching device. The handheld device includes an ultrasonic probe. The signal switching device is electrically connected to the handheld device, and the signal switching device is configured to provide a burst wave capable of generating a resonant carrier wave through a piezoelectric material to the handheld device, so that a ultrasonic wave performs a needleless delivery on a carrier.

In one embodiment of the present disclosure, the signal switching device includes a timer and a conversion module. The timer is configured to generate a clock signal. The conversion module is electrically connected to the timer, and the conversion module is based on the clock signal to convert an input voltage into the burst wave capable of generating the resonant carrier wave through the piezoelectric material.

In one embodiment of the present disclosure, the handheld device includes a probe circuit. The probe circuit is electrically connected to the ultrasonic probe.

In one embodiment of the present disclosure, the probe circuit includes an ultrasonic driver module and a plurality of matching circuits. The ultrasonic driver module is configured to receive the burst wave capable of generating the resonant carrier wave through the piezoelectric material and to generate a burst wave signal capable of generating a plurality of resonant carrier waves with a plurality of ultrasonic frequencies through a plurality of piezoelectric materials. The matching circuits are electrically connected to the ultrasonic driver module and a plurality of transducer probes, the matching circuits are configured to match impedances of the ultrasonic drive module and the transducer probes respectively, where the transducer probes are integrated into the ultrasonic probe.

In one embodiment of the present disclosure, the handheld device further includes a holder and a detachable dialysis membrane. The holder surrounds the ultrasonic probe. The detachable dialysis membrane is detachably sleeved on the holder, the detachable dialysis membrane has a perfusion area, the perfusion area is configured to accommodate the carrier and to access the ultrasonic probe.

In one embodiment of the present disclosure, the handheld device further includes a probe extension part. The probe extension part is connected to the ultrasonic probe and extends out of the holder, an end of the probe extension part is an output end, and the output end is configured to send out the carrier.

In one embodiment of the present disclosure, the handheld device further includes a grip part and a fixing part. The fixing part is connected with the grip part, the ultrasonic probe is exposed on one side of the fixing part, and the ultrasonic probe is a plane ultrasonic probe without a waveguide.

In one embodiment of the present disclosure, the ultrasonic probe is an ultrasonic probe with a needle-type waveguide.

In one embodiment of the present disclosure, the ultrasonic probe with the needle-type waveguide is an ultrasonic probe with a flexible needle-type waveguide.

In one embodiment of the present disclosure, the ultrasonic probe with the needle-type waveguide has a first end and a second end opposite to each other, and a diameter of the first end is smaller than a diameter of the second end. The handheld device further includes a sleeve-type perfusion container and a stopper. The sleeve-type perfusion container is detachably sleeved on the first end of the ultrasonic probe with the needle-type waveguide. The stopper is connected to the second end of the ultrasonic probe with the needle-type waveguide.

In one embodiment of the present disclosure, the ultrasonic probe is a planar ultrasonic probe without a waveguide, and the handheld device further includes a perfusion container, a detachable rubber membrane and a leak-proof rubber frame. The perfusion container has one side connected to the planar ultrasonic probe without the waveguide. The detachable rubber membrane detachably is disposed on another side of the perfusion container. The leak-proof rubber frame is disposed on the perfusion container and surrounds the detachable rubber membrane.

In one embodiment of the present disclosure, the handheld device further includes an atomizer. The atomizer is configured to atomize the carrier.

In one embodiment of the present disclosure, the ultrasonic probe includes a hose, a spray tube and an ultrasonic transducer. The spray tube is surrounded by the hose. The ultrasonic transducer has a hollow tubular shape, where an outer diameter of the ultrasonic transducer is smaller than an inner diameter of the hose, an inner diameter of the ultrasonic transducer is larger than an outer diameter of the spray tube, the spray tube passes through the hollow of the ultrasonic transducer, the ultrasonic transducer is disconnected from the spray tube, an ultrasonic resonant surface of the ultrasonic transducer and an outlet of the spray tube both point outward in a same direction, and the ultrasonic transducer emits the ultrasonic wave to the spray tube, so that the spray tube delivers the carrier.

In one embodiment of the present disclosure, the ultrasonic probe includes a hose, a spray tube and an endoscope. The spray tube is surrounded by the hose. The endoscope detachably is disposed on the spray tube.

Another embodiment of the present disclosure is related to an operation method of a needle free delivery system, the needle free delivery system includes a handheld device and a signal switching device, and the operation method includes steps of: using the signal switching device to provide a burst wave capable of generating a resonant carrier wave through a piezoelectric material to the handheld device, so that a ultrasonic wave of the handheld device performs a needleless delivery on a carrier.

In one embodiment of the present disclosure, the operation method further includes steps of: using the signal switching device to generate a clock signal, so as to convert an input voltage into the burst wave capable of generating the resonant carrier wave through the piezoelectric material according to the clock signal.

In one embodiment of the present disclosure, the operation method further includes steps of: using the handheld device to receive the burst wave capable of generating the resonant carrier wave through the piezoelectric material and to generate a burst wave signal capable of generating a plurality of resonant carrier waves with a plurality of ultrasonic frequencies through a plurality of piezoelectric materials.

In view of the above, with the needle free delivery system and its operation method of the present disclosure, the convenience and delivery efficiency are greatly improved.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows:

FIG. 8 is a flow chart of an operation method of the needle free delivery system according to some embodiments of the present disclosure; and

4

Figure 9A:
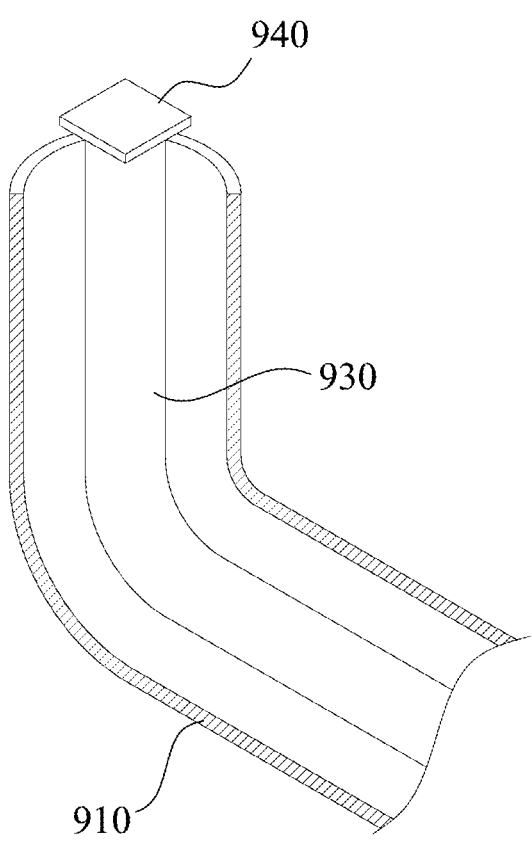
Figure 9B:
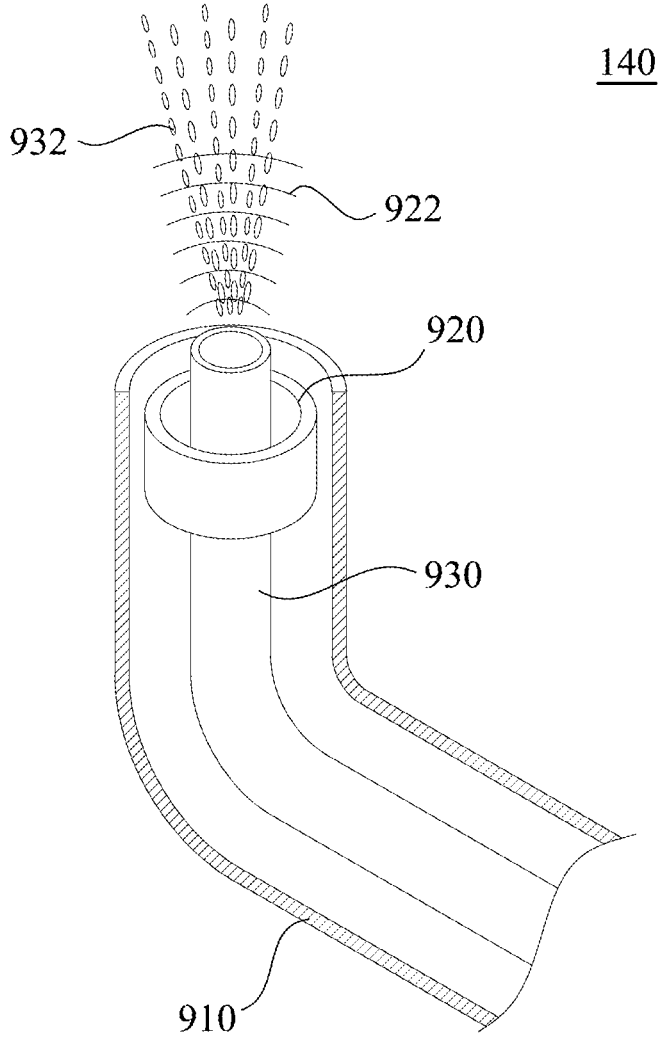

FIG. 9A and FIG. 9B are structural diagrams of an ultrasonic probe according to some embodiments of the present disclosure.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

Figure 1:
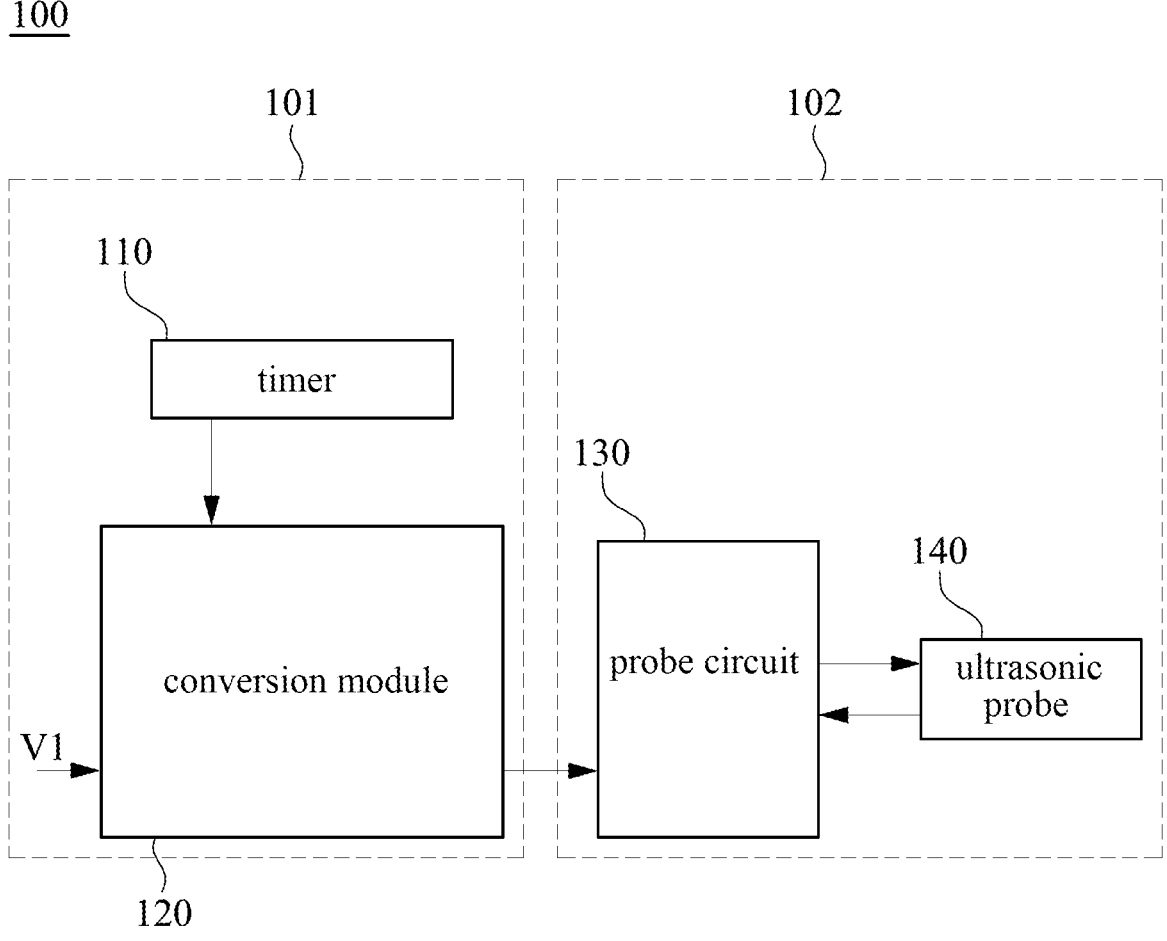
FIG. 1 is a block diagram of a needle free delivery system according to some embodiments of the present disclosure.

Referring to FIG. 1. In one aspect, the present disclosure is directed to a needle free delivery system 100. This system may be easily integrated into a needle free injector and may be applicable or readily adaptable to all technologies. Accordingly, the needle free delivery system 100 has advantages. Herewith the needle free delivery system 100 is described below with FIG. 1.

The subject disclosure provides the needle free delivery system 100 in accordance with the subject technology. Various aspects of the present technology are described with reference to the drawings. In the following description, for purposes of explanation, numerous specific details are set forth in order to provide a thorough understanding of one or more aspects. It can be evident, however, that the present technology can be practiced without these specific details. In other instances, well-known structures and devices are shown in block diagram form in order to facilitate describing these aspects. The word "exemplary" is used herein to mean "serving as an example, instance, or illustration." Any embodiment described herein as "exemplary" is not necessarily to be construed as preferred or advantageous over other embodiments.

FIG. 1 is a block diagram of the needle free delivery system 100 according to some embodiments of the present disclosure. As shown in FIG. 1, the needle free delivery system 100 includes a handheld device 102 and a signal switching device 101. In practice, for example, the handheld device 102 can be used as a lightweight handheld high-power ultrasonic needle-free injection device, which is lighter than the traditional ultrasound introducer and has higher introduction power, and it can transmit multiple frequencies at the same time. The front end of the handheld device 102 is equipped with a microbubble component carrying drugs or vaccines can effectively and safely enhance the introduction effect. The handheld device 102 can be used in otology, percutaneous absorption, dentistry or various applications that require high-power ultrasonic wave combined with the cavitation effect of microbubble to enhance local drug introduction. The front end component of the replacement probe of the handheld device 102 also can form an atomized microbubble drug carrier that is delivered deep into the trachea.

In structure, the handheld device 102 includes an ultrasonic probe 140. The signal switching device 101 is electrically connected to the handheld device 102. It should be noted that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. For example, the signal switching device 101 is built in the handheld device 102 and is directly connected to the handheld device 102, or the signal switching device 101 may be an external transformer that is indirectly connected to the processor 120 through the wired connection.

In use, the signal switching device 101 is configured to provide a burst wave capable of generating a resonant carrier wave through a piezoelectric material to the handheld device 102, so that an ultrasonic wave performs a needleless delivery on a carrier. In practice, for example, the aforementioned carrier can be a drug, a vaccine, a maintenance solution, microbubbles or other substances. For example, the aforementioned burst wave passes through the ultrasonic probe 140 containing the piezoelectric material (e.g., a piezoelectric chip) to generate the ultrasonic wave of the resonant carrier wave, but the present disclosure is not limited thereto.

In practice, for example, compared with a continuous wave, the burst wave capable of generating the resonant carrier wave through the piezoelectric material not only has a better control effect in terms of circuit temperature, but also has more favorable experimental results than the continuous wave.

For a more complete understanding of the signal switching device 101, refer to FIG. 1. In one embodiment of the present disclosure, the signal switching device 101 includes a timer 110 and a conversion module 120. In structure, the conversion module 120 is electrically connected to the timer 110. In use, the timer 110 is configured to generate a clock signal, and the conversion module 120 is based on the clock signal to convert an input voltage V1 into the burst wave capable of generating the resonant carrier wave through the piezoelectric material.

For example, the input voltage V1 may be a continuous wave, and the value of the input voltage V1 may be 30V. In a control experiment, the traditional ultrasound introducer emits continuous waves with low voltage (e.g., about 12V), resulting in low delivery efficiency. Compared with the traditional 110V AC to 12V DC power supply design, the present disclosure continuously tries to find the minimum allowable impedance value of the output control within the safe range, increases the input voltage V1 to about 30V, and obtains the maximum output power without any danger of excessive current.

In practice, for example, compared with the continuous wave, the burst wave capable of generating the resonant carrier wave through the piezoelectric material has a better breaking effect on the microbubble, so after the circuit matching is completed, the timer 110 (e.g., a 555 clock chip) and the conversion module 120 can convert the wave into the burst wave capable of generating the resonant carrier wave through the piezoelectric material and the frequency and duty cycle can be adjusted. Through the control of the duty cycle, the output is converted from a continuous wave to the burst wave capable of generating the resonant carrier wave through the piezoelectric material, and the microbubble preparation is used as a carrier to further enhance the therapeutic effect.

For a more complete understanding of handheld device 102, refer to FIG. 1. In one embodiment of the present disclosure, the handheld device 102 includes a probe circuit 130. In structure, the probe circuit 130 is electrically connected to the ultrasonic probe 140, and the conversion module 120 is electrically connected to the probe circuit 130.

In structure, for example, the conversion module 120 can be implemented by using a relay and its relay coil (which belongs to an analog circuit design), or a module having a microcontroller (which belongs to a digital TTL circuit design).

In use, for example, the timer 110 outputs a clock signal with a duty cycle of 70% and a frequency of 20 Hz, the conversion module 120 receives the clock signal, and the conversion module 120 receives the input voltage V1, so that the converter module 120 can output burst wave capable of generating the resonant carrier wave through the piezoelectric material with the duty cycle of 70% and the frequency of 20 Hz to the probe circuit 130.

Figure 2:
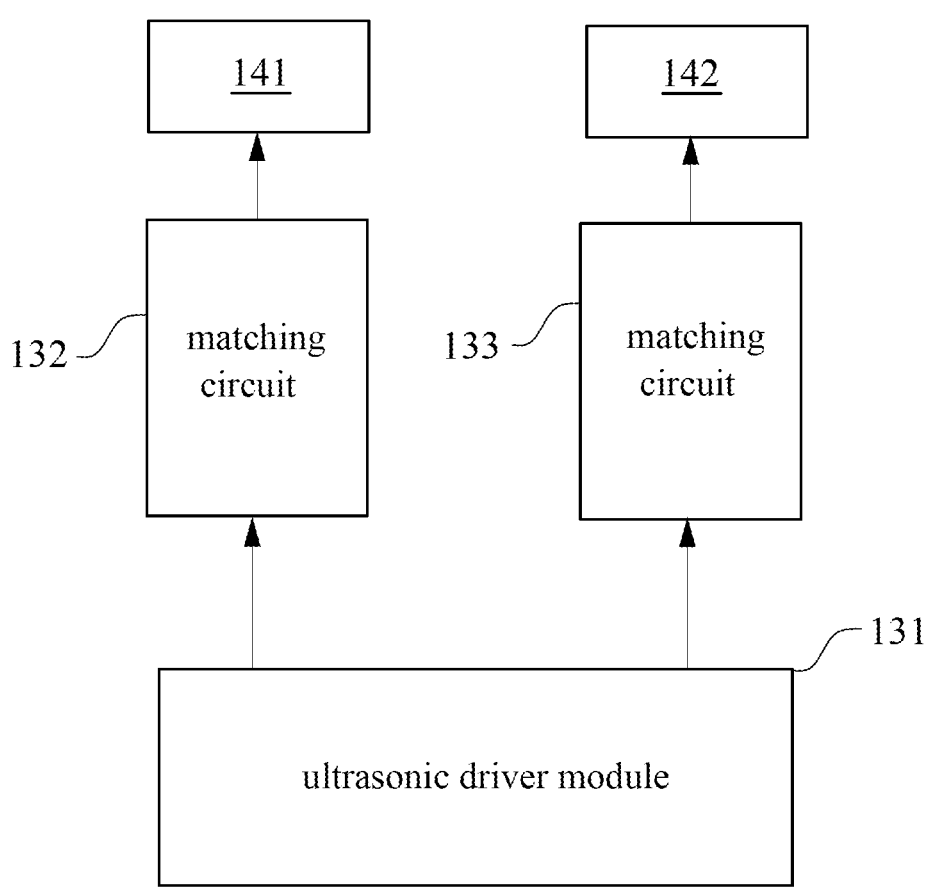
FIG. 2 is a block diagram of a multi-frequency ultrasound system according to some embodiments of the present disclosure.

As to the selection of ultrasound, in addition to the wave type, the consideration of the number of frequencies can also affect the effect. In practice, the multi-frequency ultrasound has better delivery efficiency than the single-frequency ultrasound. Therefore, the needle free delivery system 100 incorporates a multi-frequency ultrasound system to achieve better and safer outcomes. FIG. 2 is a block diagram of a multi-frequency ultrasound system 200 according to some embodiments of the present disclosure. The multi-frequency ultrasound system 200 includes an ultrasonic driver module 131 and a plurality of matching circuits 132 and 133. In structure, the matching circuits 132 and 133 are electrically connected to the ultrasonic driver module 131 and a plurality of transducer probes 141 and 142.

In use, the ultrasonic driver module 121 is configured to receive the burst wave capable of generating the resonant carrier wave through the piezoelectric material and to generate a burst wave signal capable of generating a plurality of resonant carrier waves with a plurality of ultrasonic frequencies through a plurality of piezoelectric materials, so as to achieve the transmission effect of larger carriers (e.g., drugs) with smaller sound intensity. The matching circuits 132 and 133 are configured to match impedances of the ultrasonic drive module 131 and the transducer probes 141 and 142 respectively. For example, the aforementioned burst wave signal passes through the transducer probes 141 and 142 containing the piezoelectric material to generate the ultrasonic waves of the resonant carrier waves, but the present disclosure is not limited thereto.

In practice, for example, the carrier can be microbubbles, and the dual-frequency ultrasound induces the adsorption of microbubbles with different particle sizes for improving the drug delivery efficiency and safety of the inner ear, thereby accomplishing the superiority effect of the multi-frequency ultrasound.

In practice, for example, the ultrasonic driver module 131 and the matching circuits 132 and 133 can be integrated into the probe circuit 130, and the transducer probes 141 and 142 can be integrated into the ultrasonic probe 140. In this way, the same ultrasonic probe 140 generates various frequencies, so as to enhance the cavitation effect, thereby greatly improving biological effects, such as drug delivery.

In order to modularize the ultrasonic driver module 131, in practice, for example, the ultrasonic driver module 131 and the matching circuits 132 and 133 are integrated into the probe circuit 130, and the transducer probes 141 and 142 are integrated into the ultrasonic probe 140. Therefore, the same ultrasonic probe 140 generates multi-frequencies, enhances the cavitation effect, and greatly improves biological effects such as drug delivery.

In order to avoid signal reflection of the output signal when the impedances are not matched, the matching circuits 132 and 133 are arranged between the ultrasonic driver module 131 and the transducer probes 141 and 142, thereby improving system life and safety.

In practice, for example, the transducer probes 141 and 142 can be planar transducer probes, and the material of the planar transducer probes is lead zirconate titanate (PZT) ceramic material.

For a more complete understanding of the handheld device 102, Herewith various embodiments of the handheld device 102 are described below with FIG. 3A, FIG. 3B, FIG. 4, FIG. 5, FIG. 6 and FIG. 7.

Figure 3A:
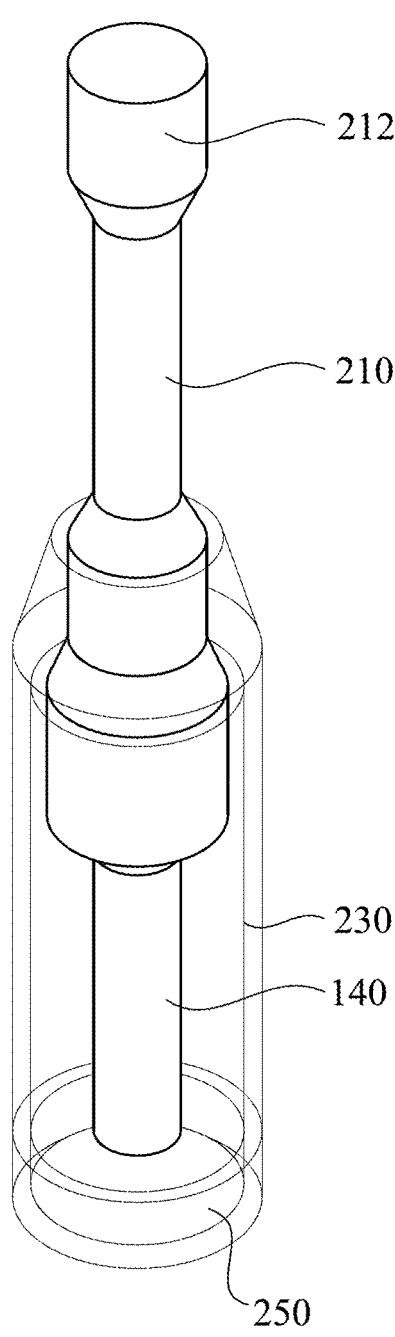
FIG. 3A is a perspective view of a handheld device in a assembled state according to a first embodiment of the present disclosure.
Figure 3B:
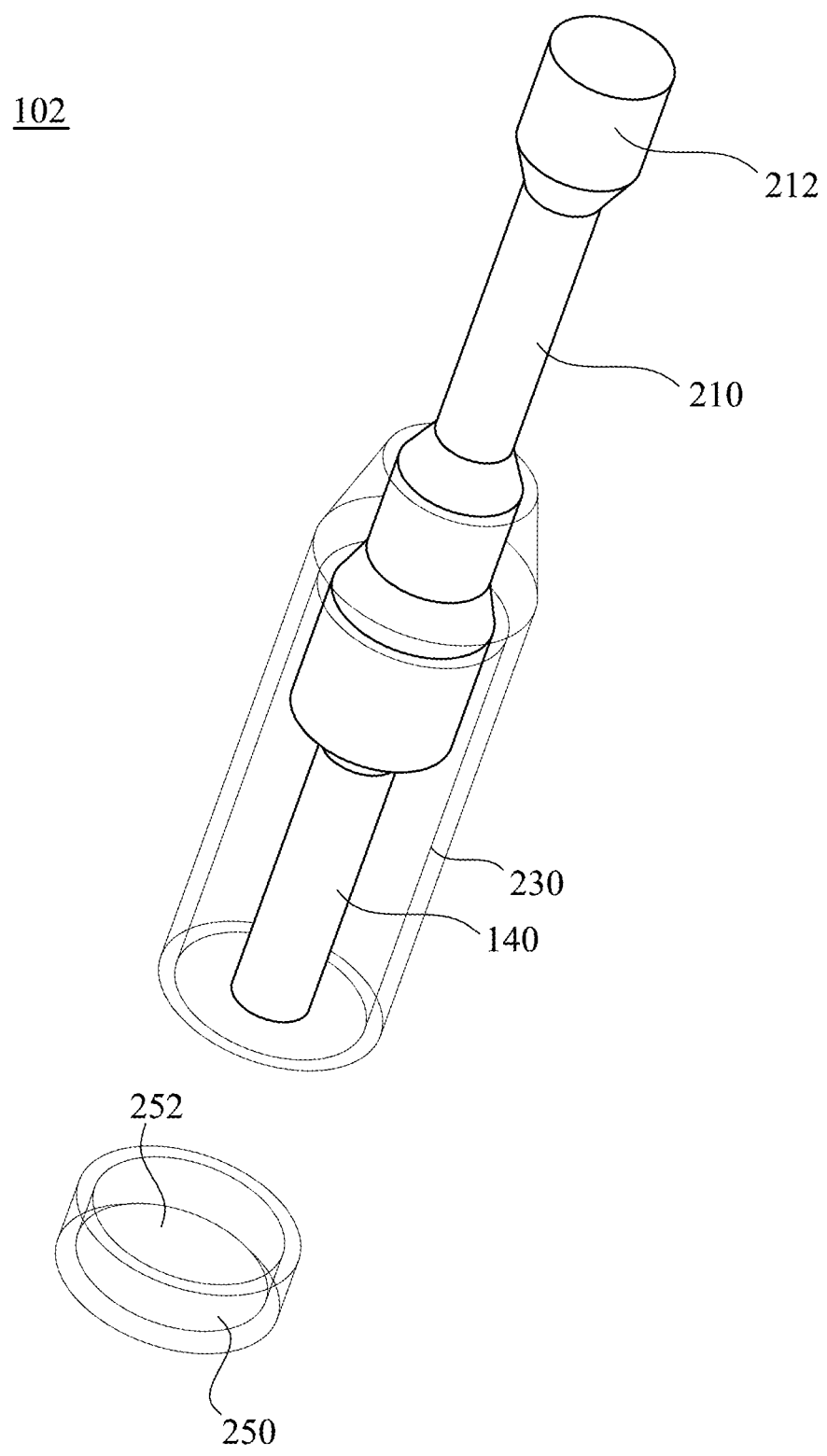
FIG. 3B is a perspective view of a handheld device in a disassembled state according to the first embodiment of the present disclosure.

Referring to FIG. 3A and FIG. 3B, FIG. 3A is a perspective view of the handheld device 102 in a assembled state according to a first embodiment of the present disclosure, and FIG. 3B is a perspective view of the handheld device 102 in a disassembled state according to the first embodiment of the present disclosure. As shown in FIG. 3A and FIG. 3B, the handheld device 102 further includes a holder 230 and a detachable dialysis membrane 250. In structure, the holder 230 surrounds the ultrasonic probe 140. The detachable dialysis membrane 250 is detachably sleeved on the holder 230, the detachable dialysis membrane 250 has a perfusion area 252, the perfusion area 252 is configured to accommodate the carrier and to access the ultrasonic probe 140.

As shown in FIG. 3A and FIG. 3B, in the first embodiment of the present disclosure, the handheld device 102 further includes a probe extension part 210. In structure, the probe extension part 210 is connected to the ultrasonic probe 140 and extends out of the holder 230, an end of the probe extension part 210 is an output end 212, and the output end 212 is configured to send out the carrier.

In practice, for example, the material of the holder 230 may be transparent acrylic, so as to provide a rigid fixing structure and facilitate the user to view the condition of the ultrasonic probe 140.

Figure 4:
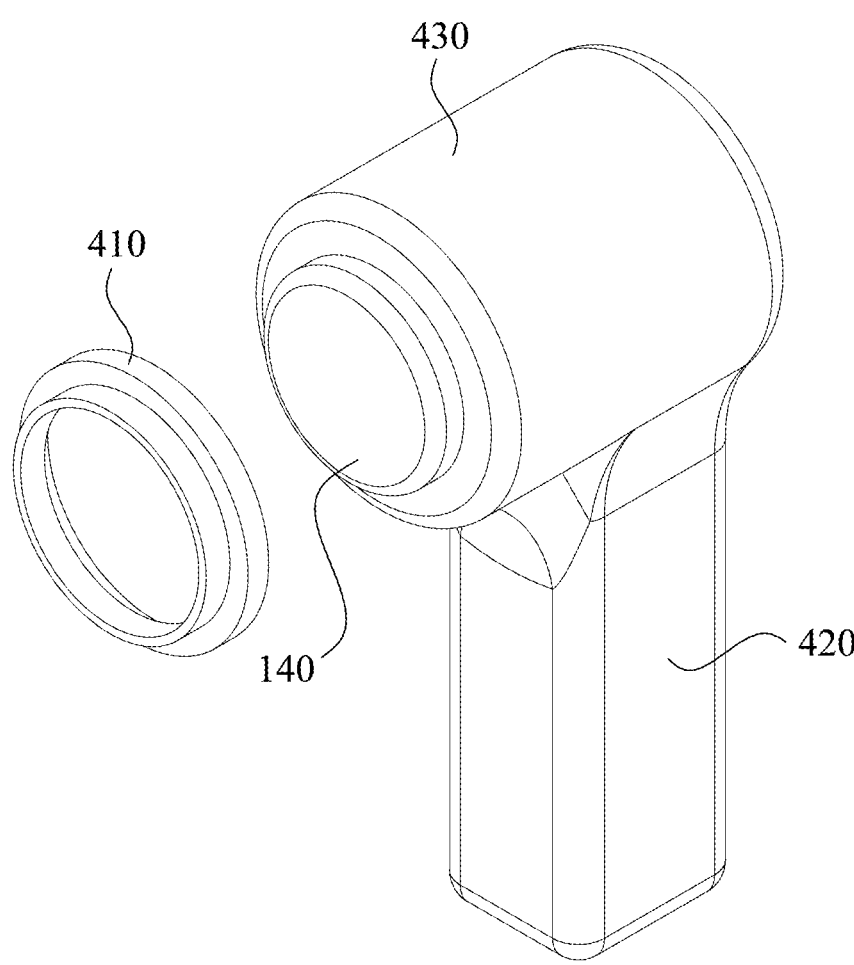
FIG. 4 is a perspective view of a handheld device according to a second embodiment of the present disclosure.

FIG. 4 is a perspective view of the handheld device 102 according to a second embodiment of the present disclosure. As shown in FIG. 4, in the second embodiment of the present disclosure, the handheld device 102 further includes a grip part 420 and a fixing part 430. In structure, the fixing part 430 is connected with the grip part 420, and the grip part 420 and the fixing part 430 can be integrally formed with each other. The ultrasonic probe 140 is exposed on one side of the fixing part 430, and the ultrasonic probe 140 is a plane ultrasonic probe without a waveguide, so that it can be easily used in aesthetic medicine or other technical aspects.

In practice, for example, the rubber frame 410 can be sleeved on the ultrasonic probe 140 to help protect the ultrasonic probe 140 and prevent leakage of the carrier. A rubber membrane (e.g., a detachable rubber membrane) can be selectively added to the fixing part 430 on the same side of the rubber frame 410 to facilitate the filling of the carrier.

Figure 5:
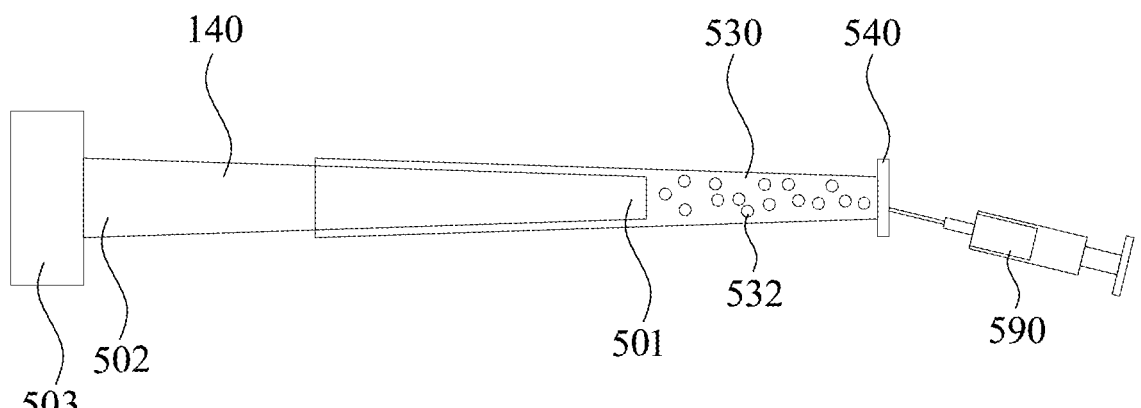
FIG. 5 is a perspective view of a handheld device according to a third embodiment of the present disclosure.

FIG. 5 is a perspective view of the handheld device 102 according to a third embodiment of the present disclosure. As shown in FIG. 5, in the third embodiment of the present disclosure, the ultrasonic probe 140 is an ultrasonic probe 140 with a needle-type waveguide. In practice, for example, the length of the ultrasonic probe 140 with the needle-type waveguide can depend on the average human ear canal length, and its value may be approximately 3 cm, and the diameter of the ultrasonic probe 140 of a needle-type waveguide can be approximately 1 to 6 mm in size.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

In practice, the human ear canal is tortuous rather than straight. Therefore, in the third embodiment of the present disclosure, the ultrasonic probe 140 with the needle-type waveguide is an ultrasonic probe 140 with a flexible needle-type waveguide, so as to easily access to the ear canal. For example, the material of the ultrasonic probe 140 with the flexible needle-type waveguide may contain fibers or other elastic materials.

As shown in FIG. 5, in the third embodiment of the present disclosure, the ultrasonic probe 140 with the needle-type waveguide has a first end 501 and a second end 502 opposite to each other. In structure, the diameter of the first end 501 is smaller than the diameter of the second end 502 to facilitate access to the ear canal. The handheld device 102 further includes a stopper 503. The stopper 503 is connected to the second end 502 of the ultrasonic probe with the needle-type waveguide, so as to prevent the entire of the ultrasonic probe 140 with the needle-type waveguide from accidentally falling into the ear.

As shown in FIG. 5, in the third embodiment of the present disclosure, the handheld device 102 further includes a sleeve-type perfusion container 530. In structure, the sleeve-type perfusion container 530 is detachably sleeved on the first end 501 of the ultrasonic probe 140 with the needle-type waveguide, and the end of the sleeve-type perfusion container 530 has a detachable rubber membrane 540. Thus, the user can use the syringe 590 to pour the carrier 532 (e.g., microbubbles) into the sleeve-type perfusion container 530 through the detachable rubber membrane 540.

Figure 6:
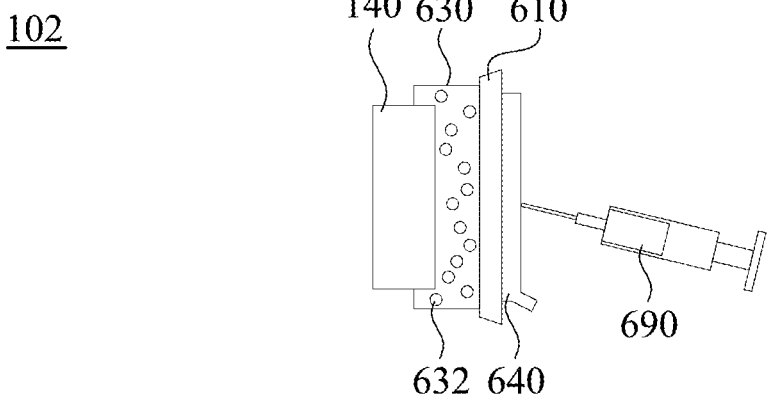
FIG. 6 is a perspective view of a handheld device according to a fourth embodiment of the present disclosure.

FIG. 6 is a perspective view of a handheld device 102 according to a fourth embodiment of the present disclosure. As shown in FIG. 6, in one embodiment of the present embodiment, the ultrasonic probe 140 is a planar ultrasonic probe 140 without a waveguide. The handheld device 102 further includes a perfusion container 630, a detachable rubber membrane 640 and a leak-proof rubber frame 610. In structure, the perfusion container 630 has one side connected to the planar ultrasonic probe 140 without the waveguide, and the detachable rubber membrane 640 is detachably disposed on another side of the perfusion container 630. The leak-proof rubber frame 610 is disposed on the perfusion container 630 and surrounds the detachable rubber membrane 640. Thus, the user can use the syringe 690 to pour the carrier 632 (e.g., microbubbles) into the perfusion container 630 through the detachable rubber membrane 640.

Figure 7:
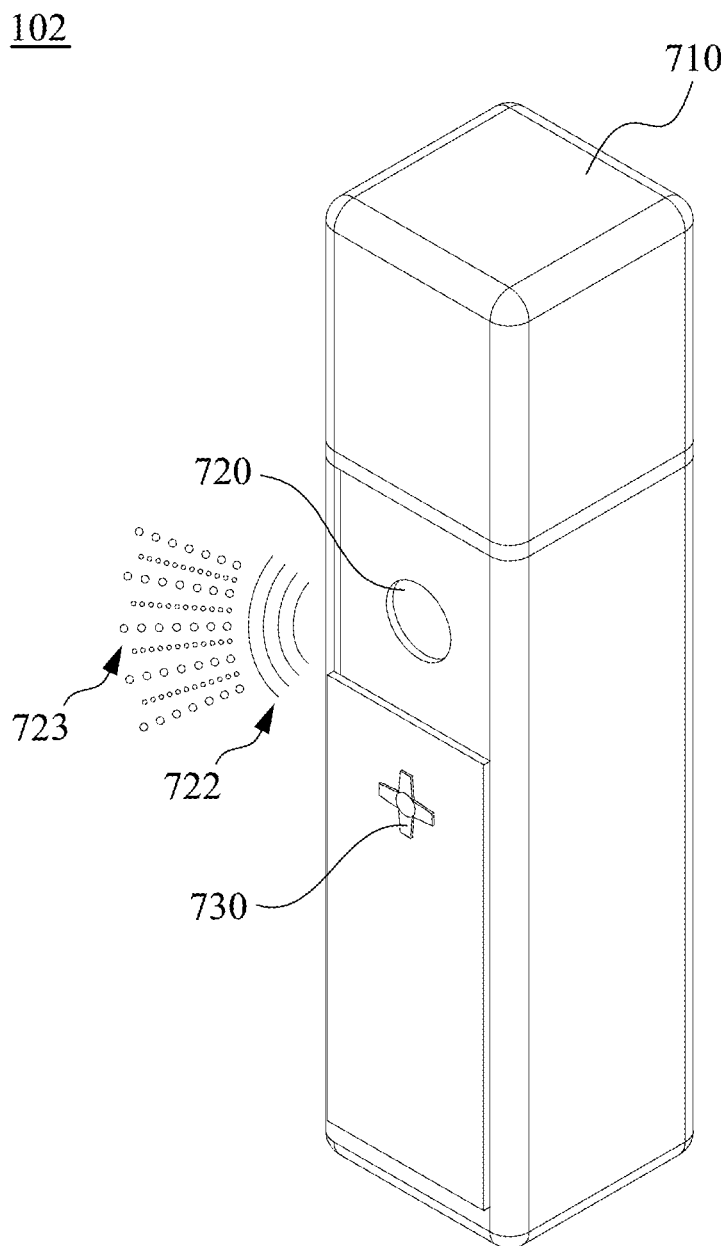
FIG. 7 is a perspective view of a handheld device according to a fifth embodiment of the present disclosure.

FIG. 7 is a perspective view of a handheld device according to a fifth embodiment of the present disclosure. As shown in FIG. 7, in one embodiment of the present embodiment, the handheld device 102 further includes a handheld device housing 710, an atomizer 720 and a control button 730. In structure, all components of the handheld device 102 in FIG. 1 can be installed in the handheld device housing 710, and the atomizer 720 and the control button 730 are disposed on the handheld device housing 710. In use, the user can operate the control button 730 to make the atomizer 720 atomize the carrier 723.

In practice, for example, the carrier 723 can be microbubbles, and the atomizer 720 can be realized by an array composed of a plurality of cone-shaped nozzles, so as to have a good atomization effect, and can also switch piezoelectric materials to generate the burst wave. Therefore, the atomizer 720 not only has the function of atomizing the carrier 723 but also can be switched to emit or synchronously emit the ultrasonic wave 722. The experimental results prove that the microbubbles leaving the atomizer 720 are still filled with gas, and the size and shape of the microbubbles are complete, indicating that the atomizer 720 cannot cause damage to the integrity of the microbubbles after atomization and cannot cause excessive losses, and many parts of the aerosol can deposit deep in the lungs. It is also found that the atomized lysozyme microbubbles had enhanced antibacterial and drug-loading properties because some of the lysozymes dissolved from the lysozyme shells into the solution during the atomization process. Thus, lysozyme microbubbles through the atomizer 720 can be used as inhalations without any loss of structural integrity or antimicrobial activity.

For a more complete understanding of an operation method performed by the needle free delivery system 100, referring FIGS. 1-8, FIG. 8 is a flow chart of an operation method 800 of the needle free delivery system 100 according to some embodiments of the present disclosure. As shown in FIG. 8, the operation method 800 includes operations S801 and S802. However, as could be appreciated by persons having ordinary skill in the art, for the steps described in the present embodiment, the sequence in which these steps is performed, unless explicitly stated otherwise, can be altered depending on actual needs; in certain cases, all or some of these steps can be performed concurrently.

In the operation method 800, the signal switching device 101 is used to provide a burst wave capable of generating a resonant carrier wave through a piezoelectric material to the handheld device 102, so that a ultrasonic wave of the handheld device 102 performs a needleless delivery on a carrier.

Specifically, in operation S801, the signal switching device 101 is used to generate a clock signal, so as to convert an input voltage into the burst wave capable of generating the resonant carrier wave through the piezoelectric material according to the clock signal, and the burst wave capable of generating a resonant carrier wave through a piezoelectric material is provided for the handheld device 102 through the signal switching device 101. In operation S802, the handheld device 102 is used to receive the burst wave capable of generating the resonant carrier wave through the piezoelectric material and to generate a burst wave signal capable of generating a plurality of resonant carrier waves with a plurality of ultrasonic frequencies through a plurality of piezoelectric materials, so that the ultrasonic probe 140 of the handheld device 102 can deliver the carrier.

FIG. 9A and FIG. 9B are structural diagrams of an ultrasonic probe 140 according to some embodiments of the present disclosure. In operation, an endoscope 940 can be replaced (as shown in FIG. 9A; confirming the correctness of the in-depth position) with an ultrasonic transducer 920 (as shown in FIG. 9B; sending ultrasound 922 to assist in drug delivery).

In one embodiment, the ultrasonic probe 140 in FIG. 9B is a soft microbubble atomizing ultrasonic probe, which includes a hose 910, an ultrasonic transducer 920 and a spray tube 930. In structure, the ultrasonic transducer 920 is a hollow tubular shape, and the outer diameter of the ultrasonic transducer 920 is smaller than the inner diameter of the hose 910, so that the hose 910 can surround the ultrasonic transducer 920. The inner diameter of the ultrasonic transducer 920 is larger than the outer diameter of the spray tube 930, so that the ultrasonic transducer 920 can surround the spray tube 930. An ultrasonic resonant surface of the ultrasonic transducer 920 and an outlet of the spray tube 930 both point outward in a same direction. In use, the ultrasonic transducer 920 emits the ultrasonic wave to the spray tube 930, so that the spray tube 930 delivers the carrier 932 (e.g., microbubbles and/or drugs).

The ultrasonic probe 140 in FIG. 9A is an endoscopic ultrasonic soft probe. In structure, the endoscope 940 is disposed on the spray tube 930. In practice, for example, the inner diameter of the ultrasonic transducer 920 in FIG. 9B is larger than that of the endoscope 940 in FIG. 9A., and the inner diameter of the ultrasonic transducer 920 is configured to circumferentially surround the endoscope 940 with a clearance gap such as when the endoscope 940 is disposed on the spray tube 930, the ultrasonic transducer 920 in FIG. 9B can be selectively removed.

In practice, for example, the ultrasonic probe 140 can be a soft bronchoscope ultrasonic probe or other types of probes. Taking the soft bronchoscope ultrasonic probe as an example, this probe can further inject atomized microbubbles and therapeutic drugs when it reaches the target, and can be combined with a needle-free ultrasonic drug delivery device (e.g., the ultrasonic transducer 920 and the spray tube 930) with diagnostic and therapeutic functions. After changing the phlegm structure in the trachea or symptom of lung by the cavitation effect, the treatment drug is given to enhance the treatment efficiency.

In view of the above, the technical solution of the present disclosure has obvious advantages and beneficial effects compared with the prior art. With the needle free delivery system 100 and the operation method 800 of the present invention, convenience and delivery efficiency are greatly improved. The needle free delivery technology of the present disclosure ensures almost painless and efficient delivery of carriers (e.g., drugs). The non-invasive, non-toxic, non-vascular injection of microbubble drug carriers combined with the sonoporation effect of the ultrasonic wave on cell membranes can successfully improve the delivery efficiency of various drugs through percutaneous or other affected parts and can reduce the dosage and side effects.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A needle free delivery system, comprising:
   a handheld device comprising an ultrasonic probe; and
   a signal switching device electrically connected to the handheld device, and the signal switching device configured to provide a burst wave capable of generating a resonant carrier wave through a piezoelectric material to the handheld device, so that a ultrasonic wave performs a needleless delivery on a carrier,
   wherein the ultrasonic probe comprises: a hose; a spray tube surrounded by the hose; and an ultrasonic transducer having a hollow, wherein an outer diameter of the ultrasonic transducer is smaller than an inner diameter of the hose, an inner diameter of the ultrasonic transducer is larger than an outer diameter of the spray tube, the spray tube passes through the hollow of the ultrasonic transducer, the ultrasonic transducer is disconnected from the spray tube, an ultrasonic resonant surface of the ultrasonic transducer and an outlet of the spray tube both point outward in a same direction, and the ultrasonic transducer emits the ultrasonic waves to the spray tube, so that the spray tube delivers the carrier.

2. The needle free delivery system of claim 1, wherein the signal switching device comprises:
   a timer configured to generate a clock signal; and
   a conversion module electrically connected to the timer, and the conversion module based on the clock signal to convert an input voltage into the burst wave capable of generating the resonant carrier wave through the piezoelectric material.

3. The needle free delivery system of claim 1, wherein the handheld device comprises:

a probe circuit electrically connected to the ultrasonic probe.

4. The needle free delivery system of claim 3, wherein the probe circuit comprises:

an ultrasonic driver module configured to receive the burst wave capable of generating the resonant carrier wave through the piezoelectric material and to generate a burst wave signal capable of generating a plurality of resonant carrier waves with a plurality of ultrasonic frequencies through a plurality of piezoelectric materials; and a plurality of matching circuits electrically connected to the ultrasonic driver module and a plurality of transducer probes, the matching circuits configured to match impedances of the ultrasonic drive module and the transducer probes respectively, wherein the transducer probes are integrated into the ultrasonic probe.

5. The needle free delivery system of claim 1, wherein the handheld device further comprises:

a holder surrounding the ultrasonic probe; and a detachable dialysis membrane detachably sleeved on the holder, the detachable dialysis membrane having a perfusion area, and the perfusion area configured to accommodate the carrier and to access the ultrasonic probe.

6. The needle free delivery system of claim 5, wherein the handheld device further comprises:

a probe extension part connected to the ultrasonic probe and extending out of the holder, an end of the probe extension part being an output end, and the output end configured to send out the carrier.

7. The needle free delivery system of claim 1, wherein the handheld device further comprises:

a grip part; and a fixing part connected with the grip part, the ultrasonic probe exposed on one side of the fixing part, and the ultrasonic probe being a plane ultrasonic probe without a waveguide.

8. The needle free delivery system of claim 1, wherein the ultrasonic probe is an ultrasonic probe with a needle-type waveguide.

9. The needle free delivery system of claim 8, wherein the ultrasonic probe with the needle-type waveguide is an ultrasonic probe with a flexible needle-type waveguide.

10. The needle free delivery system of claim 8, wherein the ultrasonic probe with the needle-type waveguide has a first end and a second end opposite to each other, and a diameter of the first end is smaller than a diameter of the second end, wherein the handheld device further comprises:

a sleeve-type perfusion container detachably sleeved on the first end of the ultrasonic probe with the needle-type waveguide; and a stopper connected to the second end of the ultrasonic probe with the needle-type waveguide.

11. The needle free delivery system of claim 1, wherein the ultrasonic probe is a planar ultrasonic probe without a waveguide, and the handheld device further comprises:

a perfusion container having one side connected to the planar ultrasonic probe without the waveguide;

a detachable rubber membrane detachably disposed on another side of the perfusion container; and a leak-proof rubber frame disposed on the perfusion container and surrounding the detachable rubber membrane.

12. The needle free delivery system of claim 1, wherein the handheld device further comprises:

an atomizer configured to atomize the carrier.

13. The needle free delivery system of claim 12, wherein the atomizer emits the ultrasonic wave.

14. An operation method of a needle free delivery system, the needle free delivery system comprising a handheld device and a signal switching device, and the operation method comprising:

using the signal switching device to provide a burst wave capable of generating a resonant carrier wave through a piezoelectric material to the handheld device, so that an ultrasonic wave of the handheld device performs a needleless delivery on a carrier, wherein an ultrasonic probe of the handheld device comprises: a hose; a spray tube surrounded by the hose; and an ultrasonic transducer having a hollow, wherein an outer diameter of the ultrasonic transducer is smaller than an inner diameter of the hose, an inner diameter of the ultrasonic transducer is larger than an outer diameter of the spray tube, the spray tube passes through the hollow of the ultrasonic transducer, the ultrasonic transducer is disconnected from the spray tube, an ultrasonic resonant surface of the ultrasonic transducer and an outlet of the spray tube both point outward in a same direction, and the ultrasonic transducer emits the ultrasonic waves to the spray tube, so that the spray tube delivers the carrier.

15. The operation method of claim 14, further comprising:

using the signal switching device to generate a clock signal, so as to convert an input voltage into the burst wave capable of generating the resonant carrier wave through the piezoelectric material according to the clock signal.

16. The operation method of claim 15, further comprising:

using the handheld device to receive the burst wave capable of generating the resonant carrier wave through the piezoelectric material and to generate a burst wave signal capable of generating a plurality of resonant carrier waves with a plurality of ultrasonic frequencies through a plurality of piezoelectric materials.

17. The operation method of claim 14, further comprising: using an atomizer to atomize the carrier.

18. The operation method of claim 17, further comprising: using the atomizer to emit the ultrasonic wave.

* * * * *